United States Patent [19]

Stirling et al.

[11] 4,444,754

[45] Apr. 24, 1984

[54] DERIVATIVES OF CLAVULANIC ACID, A PROCESS FOR THEIR PREPARATION AND THEIR USE

[75] Inventors: Irene Stirling, Reigate; Brian P. Clarke, Kingswood, both of England

[73] Assignee: Beecham Group Limited, England

[21] Appl. No.: 242,364

[22] Filed: Mar. 10, 1981

Related U.S. Application Data

[62] Division of Ser. No. 68,646, Aug. 22, 1979, Pat. No. 4,301,168.

[30] Foreign Application Priority Data

Sep. 9, 1978 [GB] United Kingdom ............... 36268/78

[51] Int. Cl.³ ............................................. A61K 35/00
[52] U.S. Cl. .................................................... 424/114
[58] Field of Search ......................................... 424/114

[56] References Cited

FOREIGN PATENT DOCUMENTS 2646003 4/1977 Fed. Rep. of Germany ... 260/245.3

Primary Examiner—Jerome D. Goldberg
Attorney, Agent, or Firm—Jacobs & Jacobs

[57] ABSTRACT

The compounds of the formula (I):

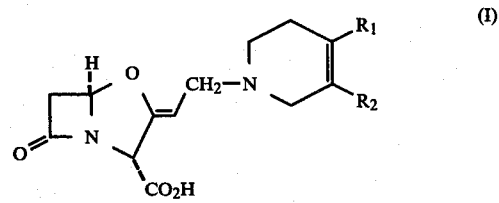

and esters thereof wherein $R_1$ is a lower alkyl group or a phenyl group and $R_2$ is a hydrogen atom or $R_2$ together with $R_1$ represents the residue of a fused benzene ring are β-lactamase inhibitors and anti-bacterial agents. Their preparation and use is described.

128 Claims, No Drawings

DERIVATIVES OF CLAVULANIC ACID, A PROCESS FOR THEIR PREPARATION AND THEIR USE

CROSS-REFERENCE

This is a division of Ser. No. 068,646 filed Aug. 22, 1979 now U.S. Pat. No. 4,301,168.

Our earlier U.S. application Ser. No. 731,928, Belgian Pat. No. 847044 and West German Offenlegungsschrift No. 26460037 disclosed derivatives of clavulanic acid in which the 9-hydroxyl group was replaced by an acylic secondary amino group. A new class of cyclic amine derivatives have now been found which have advantageous properties such as good β-lactamase inhibitory and anti-bacterial activity, crystalline form, stability and the like.

Accordingly the present invention provides the compounds of the formula (I):

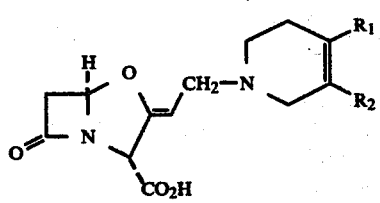

and esters thereof wherein $R_1$ is a lower alkyl group or a phenyl group and $R_2$ is a hydrogen atom or $R_2$ together with $R_1$ represents the residue of a fused benzene ring.

The compounds of this invention are preferably the parent acid of the formula (I) which generally exists as the zwitterion of the formula (II):

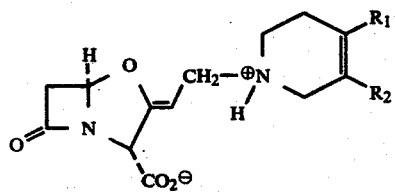

When used herein the term "lower" means a group of up to 4 carbon atoms.

Particularly suitable $R_1$ and $R_2$ in the compounds of the formulae (I) and (II) are joined to form the residue of a fused benzene ring.

Also particularly suitable $R_1$ is a phenyl group and $R_2$ is a hydrogen atom.

As has been previously indicated we prefer to prepare and use the crystalline zwitterionic compounds within the formula (II). However, esters of the compounds of the formula (II) also form part of this invention, for example as the free base or as the acid addition salt, since such compounds may also be used to enhance the effectiveness of penicillins or cephalosporins.

Certain suitable esters of the compounds of the formula (I) include those of the formula (III) and (IV):

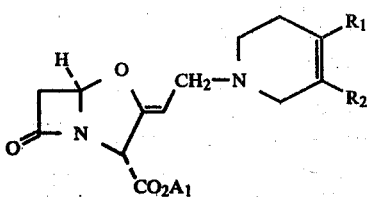

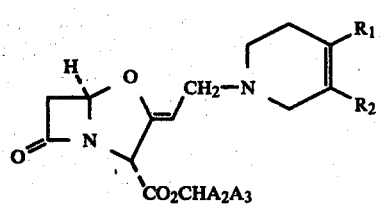

wherein $R_1$ and $R_2$ are as defined in relation to formula (II) wherein $A_1$ is an alkyl group of 1-6 carbon atoms optionally substituted by an alkoxyl or acyloxyl group of 1-7 carbon atoms; $A_2$ is an alkenyl or alkynyl group of up to 5 carbon atoms or is a phenyl group optionally substituted by a fluorine, chlorine, bromine, nitro or alkyl or alkoxyl of up to 4 carbon atoms; and $A_3$ is a hydrogen atom, an alkyl group of up to 4 carbon atoms or a phenyl group optionally substituted by a fluorine, chlorine, bromine, nitro or alkyl or alkoxyl of up to 4 carbon atoms.

Suitable esters of the compounds of the formula (II) include the methyl, ethyl, n-propyl, n-butyl, allyl, $CH_2-C\equiv CH$, methoxymethyl, acetoxymethyl, propionoxymethyl, pivaloyloxymethyl, ethoxycarbonyloxymethyl, methoxycarbonyloxyethyl, ethoxycarbonyloxyethyl, dimethoxyphthalidyl, benzyl, methoxybenzyl, ethoxybenzyl, nitrobenzyl, chlorobenzyl or the like ester.

Certain favoured groups $A_1$ include the methyl, methoxymethyl, acetoxymethyl, acetoxyethyl, phthalidyl, ethoxycarbonyloxymethyl, α-ethoxycarbonyloxyethyl and the like groups.

Certain favoured groups $A_2$ include the phenyl and 4-methoxyphenyl groups. A particularly favoured moiety $A_3$ is the hydrogen atom.

Certain other favoured values for $A_1$ include those of the sub-formulae (c), (d) and (e):

| | |
|---|---|
| $-CHA_5-OA_6$ | (c) |
| $-CHA_5-COA_6$ | (d) |
| $-CHA_5-CO_2A_6$ | (e) | wherein $A_5$ is a hydrogen atom or a methyl group and $A_6$ is an alkyl group of up to 4 carbon atoms or a phenyl or benzyl group either of which may be substituted by one or two alkyl or alkoxyl groups of up to 3 carbon atoms or by a fluorine, chlorine or bromine atom or a nitro group; or $A_5$ is joined to $A_6$ to form the residue of an unsubstituted saturated 5- or 6-membered heteroalicyclic ring or an ortho-phenylene group which may be substituted by one or two alkyl or alkoxyl groups of up to 3 carbon atoms or by a fluorine, chlorine or bromine atom or nitro group.

An apt acylic value for the sub-group of the formula (c) is $-CH_2-OA_6$.

An apt acylic value for the sub-group of the formula (d) is —CH$_2$—CO—A$_6$.

An apt acylic value for the sub-group of the formula (e) is —CH$_2$—CO$_2$A$_6$.

A further apt acylic value for the sub-group of the formula (e) is —CH(CH$_3$)—CO$_2$A$_6$.

Favoured values for A$_6$ in the preceding acylic moieties include the methyl, ethyl, propyl, butyl, phenyl and benzyl groups.

Apt cyclic values for the sub-group of the formula (c) include the tetrahydropyranyl and tetrahydrofuranyl groups.

Esters of the compounds of the formula (I) may be presented in the form of their acid addition salts if desired. The acid used to form the salt will most suitably be pharmaceutically acceptable, but non-pharmaceutically acceptable acid addition salts are also envisaged, for example as intermediates in the preparation of the pharmaceutically acceptable salts by ion exchange. Suitable pharmaceutically acceptable acid addition salts include those of inorganic and organic acids, such as hydrochloric, phosphoric, sulphuric, methanesulphonic, toluenesulphonic, citric, malic, acetic, lactic, tartaric, propionic, succinic or the like acid. Most suitably the acid addition salt is provided as a solid and preferably as a crystalline solid.

Compounds of this invention wherein crystalline form may be solvated, for example hydrated.

The present invention provides a pharmaceutical composition which comprises a compound of this invention and a pharmaceutically acceptable carrier.

The compositions of the invention include those in a form adapted for oral, topical or parenteral use and may be used for the treatment of the infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating antibiotics.

Injectable or infusable compositions of a compound of the invention are particularly suitable as high blood levels of the compound can occur after administration by injection or infusion. Thus, one preferred composition aspect of this invention comprises a compound of the invention in sterile form and most suitably in sterile crystalline form. The zwitterionic compounds of this invention are particularly suitable for use in such compositions.

The injectable solution of the compound of this invention may be made up in a sterile pyrogen-free liquid such as water, aqueous ethanol or the like.

Compounds of this invention when in highly pure crystalline form tend to have relatively low aqueous solubilities so that if it is desired to administer substantial quantities of the medicament this can require fairly large quantities of water for reconstitution. In these circumstances it is often convenient to administer the solution intravenously.

An alternative approach to administering the compounds of this invention and especially those zwitterionic compounds of the formula (II) is to utilise an injectable suspension. Such suspensions may be made up in sterile water; sterile saline or the like and may also contain suspending agents such as polyvinylpyrrolidone, lecithin or the like (for example in the manner described for amoxycillin trihydrate in Belgian Pat. No. 839109). Alternatively such compositions may be prepared in an acceptable oily suspending agent such as acharis oil or its equivalent. The use of suspensions can give rise to advantageously prolonged blood levels of the medicament. Belgian Pat. No. 839109 may be consulted for suitable methods and materials for producing injectable aqueous suspensions. For use in such suspensions the zwitterionic compound of this invention should be in the form of fine particles as described in said Belgian Patent.

Unit dose compositions comprising a compound of this invention adapted for oral administration form a further suitable composition aspect of this invention. However, orally administrable forms are generally less favoured than injectable forms owing to the relatively poor absorption of the compounds from the gastrointestinal tract. Despite this orally administrable compositions are of use as a synergistically effective blood level can be expected at high doses and at lower doses such compositions may be used to treat infections localised in the gastro-intestinal tract.

Unit dose compositions comprising a compound of this invention adapted for topical administration are also presented by this invention. In this instance 'topical administration' also includes local administration to internal surfaces of mammary glands of cattle, for example during the treatment of mastitis by intra-mammary administration.

The compound of the formula may be present in the composition as sole therapeutic agent or it may be present together with other therapeutic agents such as a penicillin or cephalosporin. Considerable advantages accrue from the inclusion of a penicillin or cephalosporin since the resulting composition shows enhanced effectiveness (synergy).

Suitable penicillins for inclusion in the compositions of this invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, and other known penicillins including pro-drugs therefore such as their in-vivo hydrolysable esters such as the acetoxymethyl, pivaloyloxymethyl, α-ethoxycarbonyloxyethyl or phthalidyl esters of ampicillin, benzylpenicillin or amoxycillin, and aldehyde or ketone adducts of penicillins containing an 6-α-aminoacetamide side chain (such as hetacillin, metampicillin and analogous derivatives of amoxycillin) or α-esters of carbenicillin or ticarcillin such as their phenyl or indanyl α-esters.

Suitable cephalosporins for inclusion in the compositions of this invention include cefatrizine, cephaloridine, cephalothin, cefazolin, cephalexin, cephacetrile, cephamandole nafate, cephapirin, cepradine, 4-hydroxycephalexin, cefaparole, cephaloglycin, and other known cephalosporins or pro-drugs thereof.

Such compounds are frequently used in the form of a salt or hydrate of the like.

Naturally if the penicillin or cephalosporin present in the composition is not suitable for oral administration then the composition will be adapted for parenteral administration. As previously indicated such injectable or infusable compositions are preferred.

Highly favoured penicillins for use in the compositions of this invention include ampicillin, amoxycillin, carbenicillin and ticarcillin. Such penicillins may be used as a pharmaceutically acceptable salt such as the sodium salt. Alternatively the ampicillin or amoxycillin may be used in the form of fine particles of the zwitterionic form (generally as ampicillin trihydrate or amoxycillin trihydrate) for use in an injectable suspension, for example, in the manner hereinbefore described for a compound of this invention.

The preferred penicillin for use in the synergistic composition is amoxycillin, for example as its sodium salt or trihydrate.

Particularly suitable cephalosporins for use in the compositions of this invention include cephaloridine and cefazolin. Such cephalosporins may be used as a pharmaceutically acceptable salt, for example the sodium salt.

When present together with a cephalosporin or penicillin, the ratio of a compound of the invention to the penicillin or cephalosporin agent may vary over a wide range of ratios, such as from 10:1 to 1:10 for example about 3:1, 2:1, 1:1, 1:2, 1:3, 1:4, 1:5 or 1:6, (wt/wt, based on pure free antibiotic equivalent). Orally administrable compositions containing a compound of the invention will normally contain relatively more synergist than corresponding injectable compositions, for example the ratio in an oral composition may be from about 3:1 to about 1:1 whereas a corresponding injectable composition may contain a ratio of about 1:1 to about 1:3 (compound of the invention: penicillin of cephalosporin).

The total quantity of a compound of the invention in any unit dosage form will normally be between 25 and 1000 mg and will usually be between 50 and 500 mg, for example about 62.5, 100, 125, 150, 200 or 250 mg.

Compositions of this invention may be used for the treatment of infections of inter alia, the respiratory tract, the urinary tract and soft tissues in humans and mastitis in cattle.

Normally between 50 and 1000 mg of the compounds of the invention will be administered each day of treatment but more usually between 100 and 750 mg of the compounds of the invention will be administered per day, for example as 1-6 doses, more usually as 2, 3 or 4 doses.

The penicillin or cephalosporin in the synergistic composition of this invention will normally be present at approximately the amount at which it is conveniently used which will usually be expected to be from about 62.5 to 1000 mg per dose, more usually about 125, 250 or 500 mg per dose.

One particularly favoured composition of this invention will contain from 150 to 1000 mg of amoxycillin as the trihydrate or sodium salt and from 25 to 500 mg of a compound of this invention.

Most suitably this form of composition will contain a compound of the formula (II).

A further particularly favoured composition of this invention will contain from 150 to 1000 mg of ampicillin or a pro-drug therefor and from 25 to 500 mg of a compound of this invention.

Most suitably this form of composition will contain ampicillin trihydrate, ampicillin anhydrate, sodium ampicillin, hetacillin, pivampicillinhydrochloride, bacampicillin hydrochloride, or talampicillin hydrochloride. Most suitably this form of the composition will contain a compound of the formula (II).

Most suitably the preceding compositions will contain from 200 to 700 mg of the penicillin component. Most suitably the preceding composition will comprise from 50 to 250 mg of a compound of the formula (II) preferably in crystalline form.

Such compositions may be adapted for oral or parenteral use except when containing an in-vivo hydrolysable ester of ampicillin or amoxycillin in which case the compositions will not be adapted for parenteral administration.

Another particularly favoured composition of this invention will contain from 200 to 2000 mg of carbenicillin, ticarcillin or a pro-drug therefor and from 50 to 500 mg of a compound of the invention.

Suitably this form of composition will contain disodium carbenicillin. Suitably this form of the composition will contain di-sodium ticarcillin.

More suitably this form of the composition will contain from 75 to 250 mg of a compound of the formula (II) preferably in crystalline form. Such compositions containing di-salts of carbenicillin and ticarcillin will be adapted for parenteral administration.

The present invention also provides a method of treating bacterial infections in humans or domestic mammals which comprises the administration of a composition of this invention.

Commonly the infection treated will be due to a strain of *Staphylococcus aureus, Streptococcus pneumoniae, Streptococcus pyogenes,* or the like. Other organisms which may be treated by an antibacterially effective amount of a compound of this invention are strains of Klebsiella and Escherichia. These other organisms named are more readily treated by using a synergistically effective amount of the compound of the invention and a penicillin or cephalosporin. The administration of the two components may take place separately but in general we prefer to use a composition containing both the synergist and the penicillin or cephalosporin.

The indications for treatment include respiratory tract and urinary tract infections in humans and mastitis in cattle.

The present invention also provides a process for the preparation of a compound of the formula (II) as hereinbefore defined or an ester thereof which process comprises the reaction of an ester of a 9-O-acyl derivative of clavulanic acid with an amine of the formula (V):

(V)

wherein $R_1$ and $R_2$ are as defined in relation to formula (I); and thereafter if desired converting the thus formed ester of the compound of the formula (I) into the compound of the formula (I):

The reaction may be carried out under the conditions described in, U.S. Ser. No. 731928, Belgian Pat. No. 847044 or West German Offenlegungsschrift No. 2646003.7 which are incorporated herein by reference.

Suitable 9-O-acyl derivatives of clavulanic acid include those described in U.S. Pat. No. 896,441 and West German Offenlegungsschrift No.P.2817085.6. A particularly suitable 9-O-acyl derivative is the 9-O-dichloroacetyl derivative.

The displacement reaction may be carried out in a dry polar non-hydroxylic organic solvent such as dimethylformamide. In general a depressed temperature is employed, for example 0°–5° C. The desired product may be obtained by dilution with ethyl acetate, washing to remove water soluble materials, drying the organic phase and evaporating under reduced pressure. The initial crude product may then be purified chormatographically for example over silica eluting with ethyl acetate.

The ester of clavulanic employed is generally one cleavable by hydrogenation, for example the benzyl ester or a substituted benzyl ester such as a nitrobenzyl, chlorobenzyl, bromobenzyl or methoxybenzyl ester. The preferred ester is the benzyl ester.

The desired compound of the formula (I) may be obtained from its hydrogenolyable ester by hydrogenation in the presence of a palladium catalyst, for example palladium on carbon. A one atmosphere pressure of hydrogen may be employed at ambient temperature.

The zwitterion may be obtained from the reaction mixture by filtering off and washing the solids and evaporating the filtrate. The resulting compound is often somewhat crude but extraction of impurities into an organic solvent such as acetonitrile can result in the production of the zwitterion in crystalline form.

Other related methods of hydrogenation which may be employed are those described in, West German Patent application No. P.28 17 085.6, Japanese Patent Application No. 48292/78 and U.S. patent application Ser. No. 896,441 which are incorporated herein by reference.

EXAMPLE 1

Benzyl 9-N-(1',2',3',4'-tetrahydroisoquinolyl)deoxyclavulanate

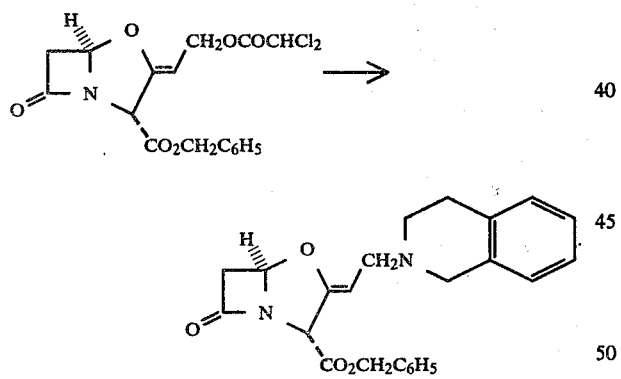

Benzyl dichloroacetyl clavulanate (5 g: 12.5 mM) in dry dimethylformamide (50 cm$^3$) at 0° C. was treated with 1,2,3,4-tetrahydroisoquinoline (1.9 equivalents) and stirred for 15 minutes. The mixture was poured into ethylacetate (250 cm$^3$) and washed with water (5×100 cm$^3$) and saturated brine (5×100 cm$^3$) dried (anhydrous magnesium sulphate) and evaporated to an oil, yield=4.7 g. 2.35 g of this crude product was chromatographed on silica eluting with ethylacetate. Fractions were collected containing the title compound Rf (SiO$_2$/ethylacetate)=0.6, combined fractions were evaporated to an oil, yield=130 mg. ν (film) 1805, 1740, 1700, 750, 700 cm$^{-1}$. δ (CDCl$_3$) 2.60–3.00 (4H, m), 3.02 (1H, d, J 17 Hz), 3.25 (2H, d, J 7 Hz), 3.46 (1H, dd, J 17 and 3 Hz), 3.56 (2H, s), 4.82 (1H, t, J 7 Hz), 5.10 (1H, s), 5.18 (2H, s), 5.67 (1H, d, J 3 Hz), 6.86–7.35 (9H, m),

EXAMPLE 2

9-N-(1,2,3,4-Tetrahydroisoquinolyl)deoxyclavulanic acid

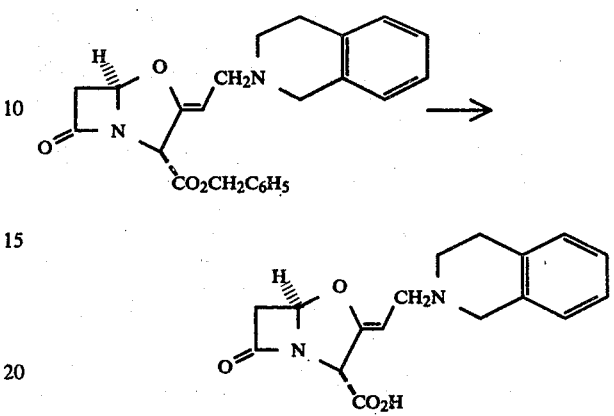

Benzyl 9-N-(1,2,3,4-tetrahydroisoquinolyl)deoxyclavulanate (125 mg; 0.34 mM) in ethanol-tetrahydrofuran (50%; 30 cm$^3$) was hydrogenolysed in the presence of 60 mg palladium on charcoal (10%), which had been pre-hydrogenated, for 25 minutes. The mixture was filtered and the catalyst washed with aqueous ethanol (50 cm$^3$). The filtrate was evaporated to an oil, to which was added acetonitrile (5 cm$^3$), a pale cream crystalline solid formed which was filtered off and washed with cold (0°) acetonitrile, then dried to give 23 mg of the title compound; Rf (SiO$_2$/butanol-propan-2-ol-water; 7:7:6)=0.5. ν(Nujol) (3700-3100), (2500-2000), 1775, 1695. 1650, 1310, 1195, 1115, 1090, 1070, 1035, 1025, 1020, 1008, 930, 915, 900, 795, 763, 750, 745, 700, 660 cm$^{-1}$. ν (KBr) (3700-3100), (2400-2000), 1770, 1690, 1625, 1498, 1452, 1434, 1370, 1308, 1190, 1114, 1035, 1017, 1005, 994, 978, 942, 930, 915, 900, 850, 824, 795, 763, 753, 744, 700, 658, 505, 465 cm$^{-1}$. δ(D$_2$O) 3.07 (1H, d, J 17 Hz), 3.0–3.63 (4H, m), 3.58 (1H, dd, J 17 and 3 Hz), 4.02 (2H, d, J 7 Hz), 4.34 (2H, s), 4.5–5.01 (2H, m), 5.73 (1H, d, J 3 Hz), 7.01–7.35 (4H, m).

EXAMPLE 3

Benzyl 9-N-(4-phenyl-1,2,3,6-tetrahydropyridyl)deoxyclavulanate

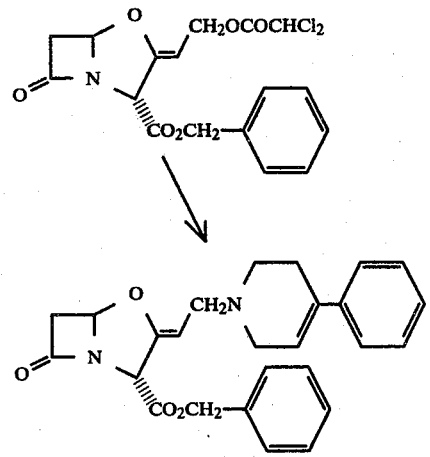

Benzyl dichloroacetalclavulanate (5.51 g: 13.8 mmol) in dimethylformamide (60 cm³) at −30° was treated with 1.9 equivalents of 4-phenyl-1,2,3,6-tetrahydropyridine in dimethylformamide (20 cm³) with stirring. Stirring was continued for ¾ hour at −30° after which the solution was poured into iced methyl acetate (250 cm³) and was washed with cold water (5×150 cm³) and saturated brine (5×150 cm³), dried (anhydrous disodium hydrogen orthophosphate) and evaporated in the presence of toluene to low volume. This crude product was chromatographed on silica eluting with methylacetate-cyclohexane (1:1). Fractions were collected containing the title compound Rf (SiO₂/methylacetate-cyclohexane; 1:1)=0.33 (detection by aqueous potassium permanganate spray), combined fractions were evaporated to yield an oil; 42 mg, ν(film) 1805, 1750, 1700 (shoulder) cm⁻¹.

EXAMPLE 4

9-N-(4-Phenyl-1,2,3,6-tetrahydropyridyl)deoxyclavulanic acid

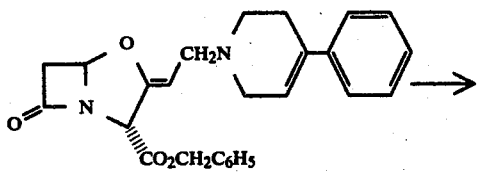

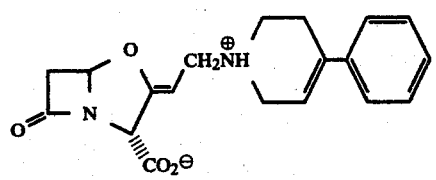

Benzyl 9-N-(4-phenyl-1,2,3,6-tetrahydropyridyl)-deoxyclavulanate (42 mg) in ethanol-tetrahydrofuran (30 cm³; 2:1) was hydrogenolysed at atmospheric pressure in the presence of palladium on carbon (20 mg) for 1 hour. The catalyst was filtered off and washed with aqueous ethanol (20 cm³) and the filtrate evaporated to an oil. This oil was chromatographed on silica eluting with ethylacetate-ethanol-water (5:2:2). Fractions were collected containing the title compound, Rf (SiO₂/ethylacetate-ethanol-water; 5:2:2)=0.65 (detection by aqueous potassium permanganate spray. Combined fractions were evaporated to yield an oil; 5.8 mg, ν (film) 1790, 1692, 1620, 750, 700 cm⁻¹. The proton magnetic resonance spectrum was consistent with the desired product.

EXAMPLE 5

Compositions (a) The compound of Example 2 (50 mgs) in sterile form may be dissolved in water for injection BP (2.5 ml) to form an injectable solution.

(b) The compound of Example 2 (50 mgs) in sterile form and sodium amoxycillin (150 mgs) in sterile form may be dissolved in water for injection BP (3.5 ml) to form an injectable solution.

Demonstration 1

The following MIC values (μg/ml) for the compound of Example 2 were obtained in DST agar containing 5% blood:

| Organism | MIC (μg/ml) |
| --- | --- |
| E. coli 0111 | 80 |
| E. coli ESS | 10 |
| E. coli JT39 (R+) | 40 |
| Kleb. aerogenes A | 20 |
| Prot. mirabilis C977 | >80 |
| Staph. aureus Oxford | ≦1.25 |
| Staph. aureus Russell | ≦1.25 |
| Staph. aureus 1517 | 20 |
| Strep. faecalis I | 80 |
| Strep. pneumoniae | ≦1.25 |
| Strep. pyogenes CN10 | ≦1.25 |

Demonstration 2

The compound of Example 2 has demonstrated good anti-bacterial activity in-vivo. When tested in mice suffering from an intraperitoneal infection of Staphylococcus aureus Smith, the following results where obtained with sub-cutaneous dosing 1 and 5 hours post infection:

| Compound | CD₅₀ (mg/kg × 2) | |
| --- | --- | --- |
| Tetrahydroisoquinolyl-deoxyclavulanic acid | 3.5 | |
| Clavulanic acid sodium | 13 | (12–27)* |

*range of results in various tests.

No overt drug induced toxicity was observed at the therapeutic dose.

The compound of Example 2 when present at 1 μg/ml reduced the in vitro MIC of ampicillin against Klebsiella aerogenes E70 from 125 μg/ml to 3.1 μg/ml and against E. coli JT39 (R$_{tem}$) from 2000 μg/ml. In an in-vivo test in mice infected intraperitoneally with E. coli E96 (R$_{tem}$) when doses sub-cutaneously 1 and 5 hours post infection the CD₅₀ of amoxycillin (mg/kg×2) was reduced from >1000 mg/kg to 22 mg/kg in the presence of 2 mg/kg of the compound of Example 2.

We claim:

1. A pharmaceutical composition useful for treating bacterial infections in mammals including humans, which comprises a synergistically effective amount of a compound of the formula I

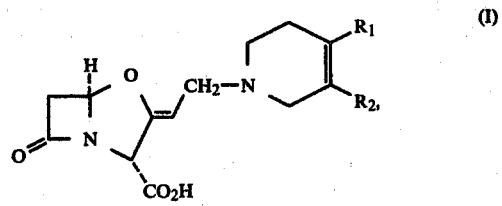

a zwitterion of the formula (II)

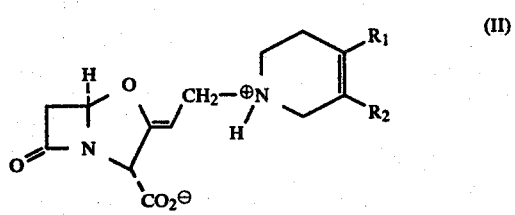

or an ester thereof, or an acid addition salt of such an ester of the formula (III) or (IV):

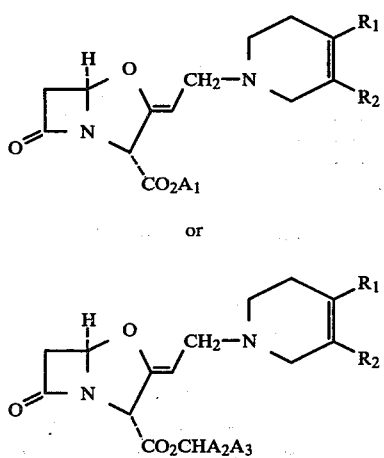

wherein $R_1$ is lower alkyl or phenyl and $R_2$ is hydrogen or $R_2$ together with $R_1$ and the carbon atoms to which they are attached form a benzene ring, $A_1$ is alkyl or 1 to 6 carbon atoms unsubstituted or substituted by alkoxyl or alkanoyloxy of 1 to 7 carbon atoms; phthalidyl, tetrahydropyranyl; or tetrahydrofuranyl; $A_2$ is alkenyl or alkynyl of up to 5 carbon atoms or phenyl unsubstituted or substituted by fluoro, chloro, bromo, nitro, alkyl of up to 4 carbon atoms or alkoxyl of up to 4 carbon atoms; and $A_3$ is hydrogen, alkyl of up to 4 carbon atoms, or phenyl unsubstituted or substituted by fluoro, chloro, bromo, nitro, alkyl of up to 4 carbon atoms or alkoxyl of up to 4 carbon atoms, and an antibacterially effective amount of a penicillin, in combination with a pharmaceutically acceptable carrier.

2. A composition according to claim 1 wherein $A_1$ is methyl, methoxymethyl, acetoxymethyl, acetoxyethyl, phthalidyl, ethoxycarbonyloxymethyl, or α-ethoxycarbonyloxyethyl.

3. A composition according to claim 1 wherein $A_2$ is phenyl or 4-methoxyphenyl.

4. A composition according to claim 1 wherein $A_3$ is hydrogen.

5. A composition according to claim 1 wherein the compound is in the form of an acid addition salt, which acide addition salt is the hydrochloride, phosphate, sulphate, methanesulphonate, toluenesulphonate, citrate, malate, acetate, lactate, tartrate, propionate, or succinate.

6. A composition according to claim 1 wherein the compound is in the form of acid addition salt and is in solid form.

7. A composition according to claim 1 wherein the compound is in the form of an acid addition salt and is in crystalline form.

8. A composition according to claim 1 wherein the compound is 9-N-(1,2,3,4-tetrahydroisoquinolyl)deoxyclavulanic acid.

9. A composition according to claim 8 wherein the penicillin is sodium amoxycillin or amoxycillin trihydrate.

10. A composition according to claim 1 wherein the compound is 9-N-(4-phenyl-1,2,3,6-tetrahydrophyridyl)deoxyclavulanic acid.

11. A composition according to claim 1 wherein the compound is in the form of the benzyl ester.

12. A composition according to claim 1 wherein the compound is the benzyl ester of 9-N-(1,2,3,4-tetrahydroisoquinolyl)deoxyclavulanic acid.

13. A composition according to claim 1 wherein the compound is the benzyl ester of 9-N-(4-phenyl-1,2,3,6-tetrahydropyridyl)deoxyclavulanic acid.

14. A composition according to claim 1 in oral administration form.

15. A composition according to claim 1 in parenteral administration form.

16. A composition according to claim 1 in topical application form.

17. A composition according to claim 1 wherein the penicillin is ampicillin, amoxycillin, carbenicillin or ticarcillin, or a pharmaceutically acceptable salt thereof.

18. A composition according to claim 1 wherein the pencillin is sodium ampicillin, sodium amoxycillin, sodium carbenicillin or sodium ticarcillin.

19. A composition according to claim 1 wherein the penicillin is amoxycillin.

20. A composition according to claim 1 wherein the penicillin is sodium amoxycillin.

21. A composition according to claim 1 wherein the penicillin is amoxycillin trihydrate.

22. A composition according to claim 1 wherein the penicillin is ampicillin trihydrate.

23. A composition according to claim 1 wherein the ratio of synergist to penicillin is from 10:1 to 1:10 wt/wt based on pure free antibiotic equivalent.

24. A composition according to claim 1 wherein the ratio of synergist to penicillin is from 3:1 to 1:6 wt/wt based on pure free antibiotic equivalent.

25. A composition according to claim 1 wherein the penicillin is benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, or an in-vivo hydrolyzable ester thereof or the ketone or aldehyde adduct thereof.

26. A pharmaceutical composition useful for treating bacterial infections in mammals including humans which comprises a synergistically effective amount of an ester of a zwitterion of the formula (II):

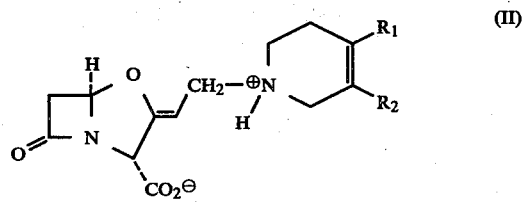

wherein $R_1$ is lower alkyl or phenyl and $R_2$ is hydrogen or $R_2$ together with $R_1$ and the carbon atoms to which they are attached form a benzene ring, which ester is the methyl, ethyl, n-propyl, n-butyl, allyl, $CH_2-C\equiv CH$, methoxymethyl, acetoxymethyl, propionoxymethyl, pivaloyloxymethyl, ethoxycarbonyloxymethyl, methoxycarbonyloxyethyl, ethoxycarbonyloxyethyl, dimethoxyphthalidyl, benzyl, methoxybenzyl, ethoxybenzyl, nitrobenzyl, or chlorobenzyl ester and an antibacterially effective amount of a penicillin, in combination with a pharmaceutically acceptable carrier.

27. A composition according to claim 26 wherein the penicillin is ampicillin, amoxycillin, carbenicillin or ticarcillin, or a pharmaceutically acceptable salt thereof.

28. A composition according to claim 26 wherein the penicillin is sodium ampicillin, sodium amoxycillin, sodium carbenicillin or sodium ticarcillin.

29. A composition according to claim 26 wherein the penicillin is amoxycillin.

30. A composition according to claim 26 wherein the penicillin is sodium amoxycillin.

31. A composition according to claim 26 wherein the penicillin is amoxycillin trihydrate.

32. A composition according to claim 26 wherein the penicillin is ampicillin trihydrate.

33. A composition according to claim 26 wherein the ratio of synergist to penicillin is from 10:1 to 1:10 wt/wt based on pure free antibiotic equivalent.

34. A composition according to claim 26 wherein the ratio of synergist to penicillin is from 3:1 to 1:6 wt/wt based on pure free antibiotic equivalent.

35. A composition according to claim 26 wherein the penicillin is benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, or an in-vivo hydrolyzable ester thereof or the ketone or aldehyde adduct thereof.

36. A pharmaceutical composition useful for treating bacterial infections in mammals including humans which comprises a synergistcally effective amount of an ester of the formula (III):

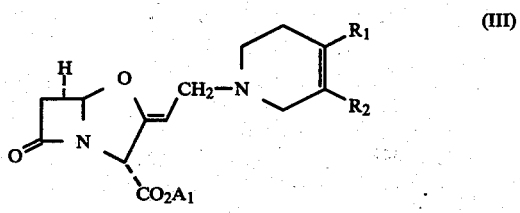

wherein
$A_1$ is of the formula (c), (d) or (e):

 (c),

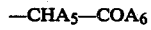 (d)

or

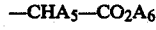 (e)

wherein $A_5$ is hydrogen or methyl, $A_6$ is alkyl of up to 4 carbon atoms, phenyl or benzyl, said phenyl or benzyl being unsubstituted or substituted by 1 or 2 alkyl or alkoxy moieties of up to 3 carbon atoms or by fluoro, chloro, bromo or nitro; or $A_5$ is joined to $A_6$ to form an ortho-phenylene moiety which ortho-phenylene ring is unsubstituted or substituted by 1 or 2 alkyl or alkoxyl moieties of up to 3 carbon atoms or by fluoro, chloro, bromo or nitro, and an antibacterially effective amount of a penicillin, in combination with a pharmaceutically acceptable carrier.

37. A composition according to claim 1 wherein $A_1$ is —$CH_2$—$OA_6$ wherein $A_6$ is alkyl of up to 4 carbon atoms or phenyl or benzyl, said phenyl or benzyl being unsubstituted or substituted by 1 or 2 alkyl or alkoxy moieties of up to 3 carbon atoms or by fluoro, chloro, bromo, or nitro.

38. A composition according to claim 37 wherein $A_6$ is methyl, ethyl, propyl, butyl, phenyl or benzyl.

39. A composition according to claim 38 wherein $A_1$ is tetrahydropyranyl or tetrahydrofuranyl.

40. A composition according to claim 1 wherein $A_1$ is —$CH_2$—CO—$A_6$ wherein $A_6$ is alkyl of up to 4 carbon atoms or phenyl or benzyl, said phenyl or benzyl being unsubstituted or substituted by 1 or 2 alkyl or alkoxyl moieties of up to 3 carbon atoms or by fluoro, chloro, bromo or nitro.

41. A composition according to claim 40 wherein $A_6$ is methyl, ethyl, propyl, butyl, phenyl or benzyl.

42. A composition according to claim 1 wherein $A_1$ is —$CH_2$—$CO_2A_6$, wherein $A_6$ is alkyl of up to 4 carbon atoms or phenyl or benzyl, said phenyl or benzyl being unsubstituted or substituted by 1 or 2 alkyl or alkoxyl moieties of up to 3 carbon atoms, or by fluoro, chloro, bromo or nitro.

43. A composition according to claim 42 wherein $A_6$ is methyl, ethyl, propyl, butyl, phenyl or benzyl.

44. A composition according to claim 1 wherein $A_1$ is —$CH(CH_3)$—$CO_2A_6$ wherein $A_6$ is alkyl of up to 4 carbon atoms or phenyl or benzyl, said phenyl or benzyl being unsubstituted or substituted by 1 or 2 alkyl or alkoxyl moieties of up to 3 carbon atoms, or by fluoro, chloro, bromo or nitro.

45. A composition according to claim 44 wherein $A_6$ is methyl, ethyl, propyl, butyl, phenyl or benzyl.

46. A composition according to claim 36 wherein the penicillin is ampicillin, amoxycillin, carbenicillin or ticarcillin, or a pharmaceutically acceptable salt thereof.

47. A composition according to claim 36 wherein the penicillin is sodium ampicillin, sodium amoxycillin, sodium carbenicillin or sodium ticarcillin.

48. A composition according to claim 36 wherein the penicillin is amoxycillin.

49. A composition according to claim 36 wherein the penicillin is sodium amoxycillin.

50. A composition according to claim 36 wherein the penicillin is amoxycillin trihydrate.

51. A composition according to claim 36 wherein the penicillin is ampicillin trihydrate.

52. A composition according to claim 36 wherein the ratio of synergist to penicillin is from 10:1 to 1:10 wt/wt based on pure free antibiotic equivalent.

53. A composition according to claim 36 wherein the ratio of synergist to penicillin is from 3:1 to 1:6 wt/wt based on pure free antibiotic equivalent.

54. A composition according to claim 36 wherein the penicillin is benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, or an in-vivo hydrolyzable ester thereof or the ketone or aldehyde adduct thereof.

55. A pharmaceutical composition useful for treating bacterial infections in mammals including humans which comprises a synergistically effective amount of a zwitterion of the formula (II):

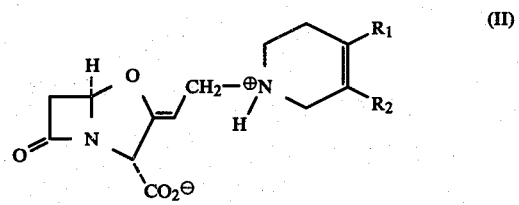

wherein R₁ is lower alkyl or phenyl and R₂ is hydrogen or R₂ together with R₁ and the carbon atoms to which they are attached form a benzene ring, in crystalline form, and an antibacterially effective amount of a penicillin, in combination with a pharmaceutically acceptable carrier.

56. A composition according to claim 55 wherein the penicillin is ampicillin, amoxycillin, carbenicillin or ticarcillin, or a pharmaceutically acceptable salt thereof.

57. A composition according to claim 55 wherein the penicillin is sodium ampicillin, sodium amoxycillin, sodium carbenicillin or sodium ticarcillin.

58. A composition according to claim 55 wherein the penicillin is amoxycillin.

59. A composition according to claim 55 wherein the penicillin is sodium amoxycillin.

60. A composition according to claim 55 wherein the penicillin is amoxycillin trihydrate.

61. A composition according to claim 55 wherein the penicillin is ampicillin trihydrate.

62. A composition according to claim 55 wherein the ratio of synergist to penicillin is from 10:1 to 1:10 wt/wt based on pure free antibiotic equivalent.

63. A composition according to claim 55 wherein the ratio of synergist to penicillin is from 3:1 to 1:6 wt/wt based on pure free antibiotic equivalent.

64. A composition according to claim 55 wherein the penicillin is benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, or an in-vivo hydrolyzable ester thereof or the ketone or aldehyde adduct thereof.

65. A method of treating bacterial infections in mammals including humans which comprises administering to such a mammal in need thereof, a synergistically effective amount of a compound of the formula (I)

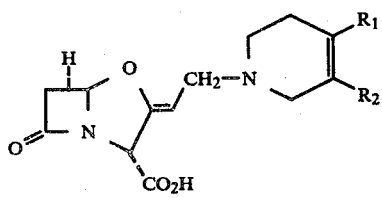

a zwitterion of the formula (II)

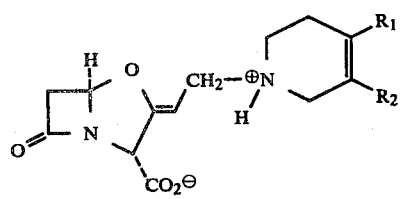

or an ester thereof, or an acid addition salt of such an ester of the formula (III) or (IV):

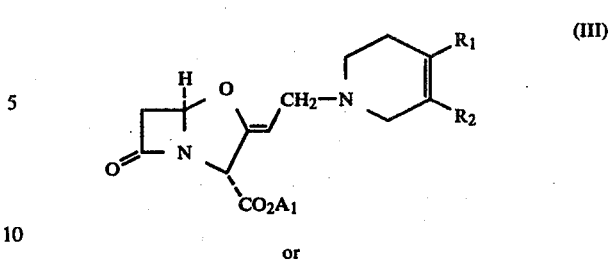

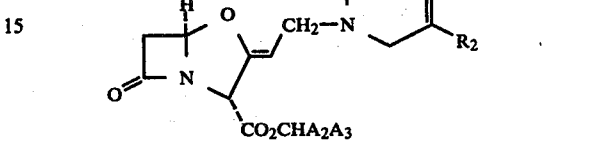

wherein R₁ is lower alkyl or phenyl and R₂ is hydrogen or R₂ together with R₁ and the carbon atoms to which they are attached form a benzene ring, A₁ is alkyl or 1 to 6 carbon atoms unsubstituted or substituted by alkoxyl or alkanoyloxy of 1 to 7 carbon atoms; or phthalidyl, tetrahydropyranyl or tetrahydrofuranyl; A₂ is alkenyl or alkynyl of up to 5 carbon atoms or phenyl unsubstituted or substituted by fluoro, chloro, bromo, nitro, alkyl of up to 4 carbon atoms or alkoxyl of up to 4 carbon atoms; and A₃ is hydrogen, alkyl of up to 4 carbon atoms, or phenyl unsubstituted or substituted by fluoro, chloro, bromo, nitro, alkyl of up to 4 carbon atoms or alkoxyl of up to 4 carbon atoms, and an antibacterially effective amount of a penicillin, in combination with a pharmaceutically acceptable carrier.

66. A method according to claim 65 wherein A₁ is methyl, methoxymethyl, acetoxymethyl, acetoxyethyl, phthalidyl, ethoxycarbonyloxymethyl, or α-ethoxycarbonyloxyethyl.

67. A method according to claim 65 wherein A₂ is phenyl or 4-methoxyphenyl.

68. A method according to claim 65 wherein wherein A₃ is hydrogen.

69. A method according to claim 64 wherein the compound is in the form of an acid addition salt, which acide addition salt is the hydrochloride, phosphate, sulphate, methanesulphonate, toluenesulphonate, citrate, malate, acetate, lactate, tartrate, propionate, or succinate.

70. A method according to claim 65, wherein the compound is in the form of an acid addition salt and is in solid form.

71. A method according to claim 65, wherein the compound is in the form of an acid addition salt and is in crystalline form.

72. A method according to claim 65 wherein the compound is 9-N-(1,2,3,4-tetrahydroisoquinolyl) deoxyclavulanic acid.

73. A method according to claim 72 wherein the penicillin is sodium amoxycillin or amoxycillin trihydrate.

74. A method according to claim 65 wherein the compound is 9-N-(4-phenyl-1,2,3,6-tetrahydrophyridyl) deoxyclavulanic acid.

75. A method according to claim 65 wherein the compound is in the form of the benzyl ester.

76. A method according to claim 65 wherein the compound is the benzyl ester of 9-N-(1,2,3,4-tetrahydroisoquinolyl) deoxyclavulanic acid.

77. A method according to claim 65 wherein the compound is the benzyl ester of 9-N-(4-phenyl-1,2,3,6-tetrahydropyridyl) deoxyclavulanic acid.

78. A method according to claim 65 wherein the administration is oral.

79. A method according to claim 65 wherein the administration is parenteral.

80. A method according to claim 65 wherein the administration is by topical application.

81. A method according to claim 65 wherein the penicillin is ampicillin, amoxycillin, carbenicillin or ticarcillin, or a pharmaceutically acceptable salt thereof.

82. A method according to claim 65 wherein the penicillin is sodium ampicillin, sodium amoxycillin, sodium carbenicillin or sodium ticarcillin.

83. A method according to claim 65 wherein the penicillin is amoxycillin.

84. A method according to claim 65 wherein the penicillin is sodium amoxycillin.

85. A method according to claim 65 wherein the penicillin is amoxycillin trihydrate.

86. A method according to claim 65 wherein the penicillin is ampicillin trihydrate.

87. A method according to claim 65 wherein the ratio of synergist to penicillin is from 10:1 to 1:10 wt/wt based on pure free antibiotic equivalent.

88. A method according to claim 65 wherein the ratio of synergist to penicillin is from 3:1 to 1:6 wt/wt based on pure free antibiotic equivalent.

89. A method according to claim 65 wherein the penicillin is benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, or an in-vivo hydrolyzable ester thereof or the ketone or aldehyde adduct thereof.

90. A method of treating bacterial infections in mammals including humans which comprises administering to such a mammal in need thereof, a synergistically effective amount of an ester of a zwitterion of the formula (II):

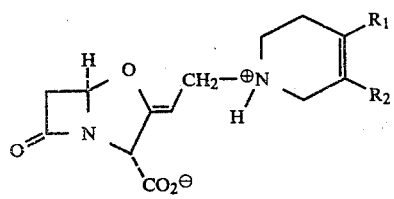

(II)

wherein R₁ is lower alkyl or phenyl and R₂ is hydrogen or R₂ together with R₁ and the carbon atoms to which they are attached form a benzene ring, which ester is the methyl, ethyl, n-propyl, n-butyl, allyl, CH₂—C≡CH, methoxymethyl, acetoxymethyl, propionoxymethyl, pivaloyloxymethyl, ethoxycarbonyloxymethyl, methoxycarbonyloxyethyl, ethoxycarbonyloxyethyl, dimethoxyphthalidyl, benzyl, methoxybenzyl, ethoxybenzyl, nitrobenzyl, or chlorobenzyl ester and an antibacterially effective amount of a penicillin, in combination with a pharmaceutically acceptable carrier.

91. A method according to claim 90 wherein the penicillin or ampicillin, amoxycillin, carbenicillin or ticarcillin, or a pharmaceutically acceptable salt thereof.

92. A method according to claim 90 wherein the penicillin is sodium ampicillin, sodium amoxycillin, sodium carbenicillin or sodium ticarcillin.

93. A method according to claim 90 wherein the penicillin is amoxycillin.

94. A method according to claim 90 wherein the penicillin is sodium amoxycillin.

95. A method according to claim 90 wherein the penicillin is amoxycillin trihydrate.

96. A method according to claim 90 wherein the penicillin is ampicillin trihydrate.

97. A method according to claim 90 wherein the ratio of synergist to penicillin is from 10:1 to 1:10 wt/wt based on pure free antibiotic equivalent.

98. A method according to claim 90 wherein the ratio of synergist to penicillin is from 3:1 to 1:6 wt/wt based on pure free antibiotic equivalent.

99. A method according to claim 90 wherein the penicillin is benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, or an in-vivo hydrolyzable ester thereof or the ketone or aldehyde adduct thereof.

100. A method of treating bacterial infections in mammals including humans which comprises administering to such a mammal in need thereof, a synergistically effective amount of an ester of the formula (III):

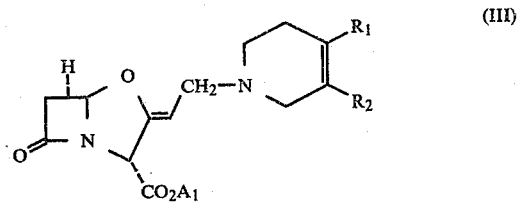

(III)

A₁ is of the formula (c), (d) or (e):

—CHA₅—OA₆ (c)

—CHA₅—COA₆ (d)

or

—CHA₅—CO₂A₆ (e)

wherein A₅ is hydrogen or methyl, A₆ is alkyl of up to 4 carbon atoms or phenyl or benzyl, said phenyl or benzyl being unsubstituted or substituted by 1 or 2 alkyl or alkoxyl moieties of up to 3 carbon atoms or by fluoro, chloro, bromo or nitro; or A₅ is joined to A₆ to form an ortho-phenylene moiety which ortho-phenylene ring is unsubstituted or substituted by 1 or 2 alkyl or alkoxyl moieties of up to 3 carbon atoms or by fluoro, chloro, bromo or nitro, and an antibacterially effective amount of a penicillin, in combination with a pharmaceutically acceptable carrier.

101. A method according to claim 100 wherein A₁ is —CH₂—OA₆ wherein A₆ is alkyl of up to 4 carbon atoms or phenyl or benzyl, said phenyl or benzyl being unsubstituted or substituted by 1 or 2 alkyl or alkoxyl moieties of up to 3 carbon atoms or by fluoro, chloro, bromo, or nitro.

102. A method according to claim 101 wherein wherein $A_6$ is methyl, ethyl, propyl, butyl, phenyl or benzyl.

103. A method according to claim 102 wherein wherein $A_1$ is tetrahydropyranyl or tetrahydrofuranyl.

104. A method according to claim 100 wherein $A_1$ is —$CH_2$—CO—$A_6$ wherein $A_6$ is alkyl of up to 4 carbon atoms or phenyl or benzyl, said phenyl or benzyl being unsubstituted or substituted by 1 or 2 alkyl or alkoxyl moieties of up to 3 carbon atoms or by fluoro, chloro, bromo or nitro.

105. A method according to claim 104 wherein $A_6$ is methyl, ethyl, propyl, butyl, phenyl or benzyl.

106. A method according to claim 100 wherein $A_1$ is —$CH_2$—$CO_2A_6$, wherein $A_6$ is alkyl of up to 4 carbon atoms or phenyl or benzyl, said phenyl or benzyl being unsubstituted or substituted by 1 or 2 alkyl or alkoxyl moieties of up to 3 carbon atoms, or by fluoro, chloro, bromo or nitro.

107. A method according to claim 106 wherein $A_6$ is methyl, ethyl, propyl, butyl, phenyl or benzyl.

108. A method according to claim 100 wherein $A_1$ is —$CH(CH_3)$—$CO_2A_6$ wherein $A_6$ is alkyl of up to 4 carbon atoms or phenyl or benzyl, said phenyl or benzyl being unsubstituted or substituted by 1 or 2 alkyl or alkoxyl moieties of up to 3 carbon atoms, or by fluoro, chloro, bromo or nitro.

109. A method according to claim 108 wherein $A_6$ is methyl, ethyl, propyl, butyl, phenyl or benzyl.

110. A method according to claim 100 wherein the penicillin is ampicillin, amoxycillin, carbenicillin or ticarcillin, or a pharmaceutically acceptable salt thereof.

111. A method according to claim 100 wherein the penicillin is sodium ampicillin, sodium amoxycillin, sodium carbenicillin or sodium ticarcillin.

112. A method according to claim 100 wherein the penicillin is amoxycillin.

113. A method according to claim 100 wherein the penicillin is sodium amoxycillin.

114. A method according to claim 100 wherein the penicillin is amoxycillin trihydrate.

115. A method according to claim 100 wherein the penicillin is ampicillin trihydrate.

116. A method according to claim 100 wherein the ratio of synergist to penicillin is from 10:1 to 1:10 wt/wt based on pure free antibiotic equivalent.

117. A method according to claim 100 wherein the ratio of synergist to penicillin is from 3:1 to 1:6 wt/wt based on pure free antibiotic equivalent.

118. A method according to claim 100 wherein the penicillin is benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, or an in-vivo hydrolyzable ester thereof or the ketone or aldehyde adduct thereof.

119. A method of treating bacterial infections in mammals including humans which comprises administering to such a mammal in need thereof, a synergistically effective amount of a zwitterion of the formula (II):

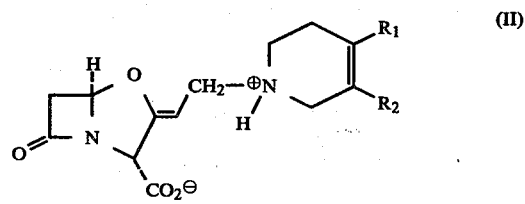

wherein $R_1$ is lower alkyl or phenyl and $R_2$ is hydrogen or $R_2$ together with $R_1$ and the carbon atoms to which they are attached form a benzene ring, in crystalline form, and an antibacterially effective amount of a penicillin, in combination with a pharmaceutically acceptable carrier.

120. A method according to claim 119 wherein the penicillin is ampicillin, amoxycillin, carbenicillin or ticarcillin, or a pharmaceutically acceptable salt thereof.

121. A method according to claim 119 wherein the penicillin is sodium ampicillin, sodium amoxycillin, sodium carbenicillin or sodium ticarcillin.

122. A method according to claim 119 wherein the penicillin is amoxycillin.

123. A method according to claim 119 wherein the penicillin is sodium amoxycillin.

124. A method according to claim 119 wherein the penicillin is amoxycillin trihydrate.

125. A method according to claim 119 wherein the penicillin is ampicillin trihydrate.

126. A method according to claim 119 wherein the ratio of synergist to penicillin is from 10:1 to 1:10 wt/wt based on pure free antibiotic equivalent.

127. A method according to claim 119 wherein the ratio of synergist to penicillin is from 3:1 to 1:6 wt/wt based on pure free antibiotic equivalent.

128. A method according to claim 119 wherein the penicillin is benzylpenicillin, phenoxymethylpenicillin, carbenicillin, azodicillin, propicillin, ampicillin, amoxycillin, epicillin, ticarcillin, cyclacillin, pirbenicillin, azlocillin, mezlocillin, celbenicillin, or an in-vivo hydrolyzable ester thereof or the ketone or aldehyde adduct thereof.

* * * * *